United States Patent [19]

Peters et al.

[11] Patent Number: 4,807,628
[45] Date of Patent: Feb. 28, 1989

[54] METHOD AND APPARATUS FOR STORING, DISPENSING, AND APPLYING SURGICAL STAPLES

[75] Inventors: Rudolph Peters; Ronald L. Peters; William Taylor, all of Oakland, Calif.

[73] Assignee: Edward Weck & Company, Inc., Research Triangle Park, N.C.

[21] Appl. No.: 727,760

[22] Filed: Apr. 26, 1985

[51] Int. Cl.$^4$ .......................... A61B 17/04; B31B 1/00
[52] U.S. Cl. .................................. 128/334 R; 227/19; 227/DIG. 1; 124/53
[58] Field of Search ....... 128/334 R; 227/19, DIG. 1; 124/34, 31

[56] References Cited

U.S. PATENT DOCUMENTS

| 3,650,453 | 3/1972 | Smith, Jr. | 227/19 |
| 4,043,504 | 8/1977 | Hueil et al. | 227/19 |
| 4,331,227 | 5/1982 | Green | 128/334 R |
| 4,391,402 | 9/1983 | Campbell et al. | 128/334 R |
| 4,410,125 | 10/1983 | Noiles et al. | 128/334 R |
| 4,470,532 | 9/1984 | Froehlich | 128/334 R |
| 4,478,362 | 10/1984 | Foslien | 227/19 |

FOREIGN PATENT DOCUMENTS

WO80/00230 2/1980 PCT Int'l Appl. .................. 227/19

OTHER PUBLICATIONS

U.S. Surgical Corporation, *Skin and Fascia*, 1974, Sep.

*Primary Examiner*—Richard C. Pinkham
*Assistant Examiner*—Gary Jackson
*Attorney, Agent, or Firm*—Harris Zimmerman; Howard Cohen

[57] ABSTRACT

A method and apparatus for storing and automatically dispensing and applying surgical staples in serial fashion includes a pistol-like tool having means for storing a large plurality of staples in parallel, stacked column fashion aligned along the longitudinal (barrel) axis of the tool. A form tool and an anvil tool extend longitudinally parallel to the axis, and are advanced in synchronism by actuation of a trigger lever. The form tool includes a pair of arms which impinge upon and rotate the legs of the staple about the web portion thereof to dispose the staple in a points-first dispensing orientation. The form tool advances the staple to the distal dispensing end of the tool, where it drives the staple into a portion of the anvil and crimps the staple thereabout. Release of the trigger causes an elevator member to separate the next distal staple in the column from its column alignment into postion to be engaged by the anvil tool and form tool at the start of the subsequent dispensing cycle. A trigger actuation mechanism prevents release of the trigger lever until the dispensed staple is completely crimped in the tissue.

45 Claims, 11 Drawing Sheets

FIG_6

FIG_7

FIG_8

FIG_12

FIG_10

FIG_11

FIG_13 FIG_14 FIG_15 FIG_16 FIG_17 FIG_18

FIG_19

FIG_20

FIG_21

FIG_22

FIG_23

METHOD AND APPARATUS FOR STORING, DISPENSING, AND APPLYING SURGICAL STAPLES

BACKGROUND OF THE INVENTION

Of the many significant innovations of modern medical practice, one of the most enduring is the use of sutures to close and secure surgical and traumatic wounds and the like. Although suturing techniques have been refined through the years, the basic needle and thread sewing approach has remained until recent times.

In the past few years, surgical staples have been introduced to replace the use of sutures in many wound closure situations. Surgical stapls offer the potential of important improvements over the suture art. For example, many staples can be delivered and applied by one surgical stapling tool in quick succession, thus greatly hastening the closure of a wound. Also, surgical stapling tools apply the same amount of bending and crimping to each staple, so that the tension applied thereby across the wound closure is uniform with each staple application. As a result, scarring may be minimized. In contrast, each suture is generally secured to a separate needle, requiring a great amount of manual work to grasp each needle, form the stitch, tie off the suture, and trim the excess suture thread. Also, the tension of each suture may vary significantly, causing puckering and uneven scar formation.

However, the techniques of surgical stapling have not gained immediate acceptance, due primarily to the shortcomings of the prior art surgical stapling tools. One significant drawback in general is that the tools now available do not provide clear visualization of the intended placement of the staples, due to the configuration and bulk of the tools themselves. Thus the surgeon must approximate the placement of each staple, and this uncertainty is unacceptable.

Also, those prior art tools which store a large number of staples do so by arranging the staples in parallel, stacked column fashion, with the column generally extending toward the dispensing end of the tool. Generally one of these staples is separated from the column and crimped about an anvil member to drive the staple legs into opposed sides of the wound to be closed. However, the staple cannot travel far from the column before being crimped without requiring a mechanism which is unwieldy and visually obstructive. That is, the legs of the staple cannot be extended far enough to be seen clearly before the crimping step begins. As a result, the visualization problem noted above is exacerbated.

Some of the surgical stapling tools developed in the prior art have attempted to overcome this problem by storing the staples in single file, points-first orientation, either in a feed channel or secured to an endless belt which advances about rollers. In either case, the utilization of storage space is poor, and few staples can be stored in one tool. As a result either the tool must be resupplied frequently, diluting the advantage of speed in application, or several disposable tools must be used, creating an unwarranted expense. Thus this approach has also proved to be unacceptable as a common medical practice.

Any surgical stapling tool must be configured to be grasped and operated easily, and this factor has led to the use of either pistol-like designs or ring-handle, scissor- or plier-type tools. With either design approach it is difficult to rotate the tool about the longitudinal axis to apply staples at any angle about the nominal line of sight of the surgeon. Some tools are provided with dispensing head ends which rotate about the longitudinal axis, but the rotational freedom is generally limied. In some tools commercially available, the dispensing head rotates eccentrically about the axis, requiring that the surgeon continually adjust to the changing offset between the barrel axis and the delivery point of the tool. This factor has also served to discourage the use of surgical staples in place of sutures.

SUMMARY OF THE PRESENT INVENTION

The present invention generally comprises a method and apparatus for storing, dispensing, and applying surgical staples to close a wound. A significant feature of the tool of the invention is that it stores a large plurality of staples in parallel, stacked column fashion, and includes means for rotating a staple to be dispensed into a points-first orientation for delivery generally parallel to the axis of the column. Thus the tool may be configured in a narrow, longitudinally tapering design to provide clear visualization of the dispensing end of the tool.

Furthermore, the tool of the present invention includes means for advancing the staple to be dispensed to the distal delivery end of the tool, so that the staple legs extend virtually completely from the delivery end before the crimping step begins. Thus the surgeon can precisely determine the points of entry of the staple legs prior to application.

The tool includes a pistol-like handle and an opposed trigger-like actuating lever, and a "barrel" portion extending obliquely to the handle portion. A dispensing head is rotatably secured to the distal end of the barrel portion, and is rotatable coaxially about the longitudinal axis of the barrel portion. Thus surgical staples may be applied at any angle about the barrel axis, while the hand wielding the tool remains in a comfortable and nonrotated dispostion.

In the rotatable dispensing head, a form tool and an anvil tool extend longitudinally in adjacent channels for reciprocal translation therealong in synchronized movement. The distal end of the anvil tool includes a flange which engages the medial web portion of the distal-most staple disposed in a dispensing position. The distal end of the form tool includes a pair of spaced arms which are disposed to impinge on the legs of the staple in the dispensing position and rotate the staple into a points - first orientation along the longitudinal axis as the form tool initially advances toward the distal end. A pair of driving surfaces adjacent to the arms then engage distal web portions of the staple in opposed relationship to the anvil flange. The form tool and the anvil tool then advance the staple along a generally linear feed path to the dispensing end of the tool.

The tool includes a staple elevator member which extends into the feed path and is disposed in a channel extending obliquely to the longitudinal axis. The elevator member includes a ramped camming surface adapted to be contacted by the staple translating along the feed path, the elevator member being driven to translate in its channel out of the feed path. The staple then advances to the distal delivery end of the tool, and the legs extend virtually completely from the delivery end.

A stop is provided for the anvil tool, while the form tool continues to advance toward the delivery end. The driving surfaces of the form tool crimp the web portion of the staple about the anvil flange, causing the staple legs to bend into confronting relationship with the points in proximate opposition. This action sets the staple in place, joining the opposed sides of the wound, or the like.

As the form tool and anvil begin to retract after the staple is applied, a finger-like ejector spring engages the medial web portion of the staple and releases the engagement of the anvil flange with the web portion. The applied staple is thus separated from the tool mechanism without any special effort by the surgeon. Further retraction of the form tool and anvil tool opens the feed path to allow the elevator member to be moved into the feed path by resilient restoring force. The column of staples is constantly urged toward the distal end by an independent elastic drive arrangement, so that the elevator member engages the next distal staple of the column. The elevator member shears and separates the next distal staple from the column, translating it obliquely to the longitudinal axis and placing it in the dispensing position. The next distal staple is thus disposed to be engaged by the form tool and the anvil tool at the beginning of the subsequent dispensing cycle.

Another significant feature of the invention is the provision of a trigger actuating mechanism which drives the form tool and anvil tool, and which minimizes jamming and misfeeding of the staples. The trigger lever extends from a trigger plate which includes at least a pair of gliding knobs disposed in longitudinally spaced relationship along an axis oblique to the extent of the trigger lever. Each of the knobs is disposed in a respective channel for sliding translation thereafter as the lever is squeezed manually. The distal-most channel is disposed parallel to the longitudinal axis, the gliding knob secured therein being linked to the form tool to drive the latter longitudinally as the trigger lever is squeezed.

The proximal gliding knob includes a toggle stop member rotatably secured thereto and operatively engaged with the respective channel. The stop member includes a friction surface, and is biased resiliently to rotate and engage the friction surface with the channel surface to prevent translation in the reverse direction as the trigger lever is squeezed. At one end of the proximal channel a camming surface on the stop member engages the channel surface to toggle the stop member past an unstable position and release the frictional engagement. The trigger lever is then free to return to the initial, quiescent position. At the other end of the proximal channel, another camming surface of the stop member is engaged by the channel surface to reset the toggle for the next dispensing cycle. Thus the trigger lever must undergo a complete actuation excursion before it will return to the initial position, and must be fully released before the next dispensing cycle can be initiated. As a result, the trigger mechanism cannot cause a partial dispensing cycle, and misfeeding and jamming problems are minimized.

DESCRIPTION OF THE PREFERRED EMBODIMENT

The present invention generally comprises a method and apparatus for storing, dispensing, and applying surgical staple clips for wound closure purposes and the like. The apparatus includes a tool featuring automatic staple feed from a large magazine, complete extension of the staple from the tool prior to initiation of crimping of the staple, positive crimping action about an anvil to set all staples uniformly, ejector means for separating a crimped staple from the tool, and trigger actuating means which requires a full actuating excursion of the trigger lever before it may begin to return to the unactuated position.

Figures 1, 2, 3:
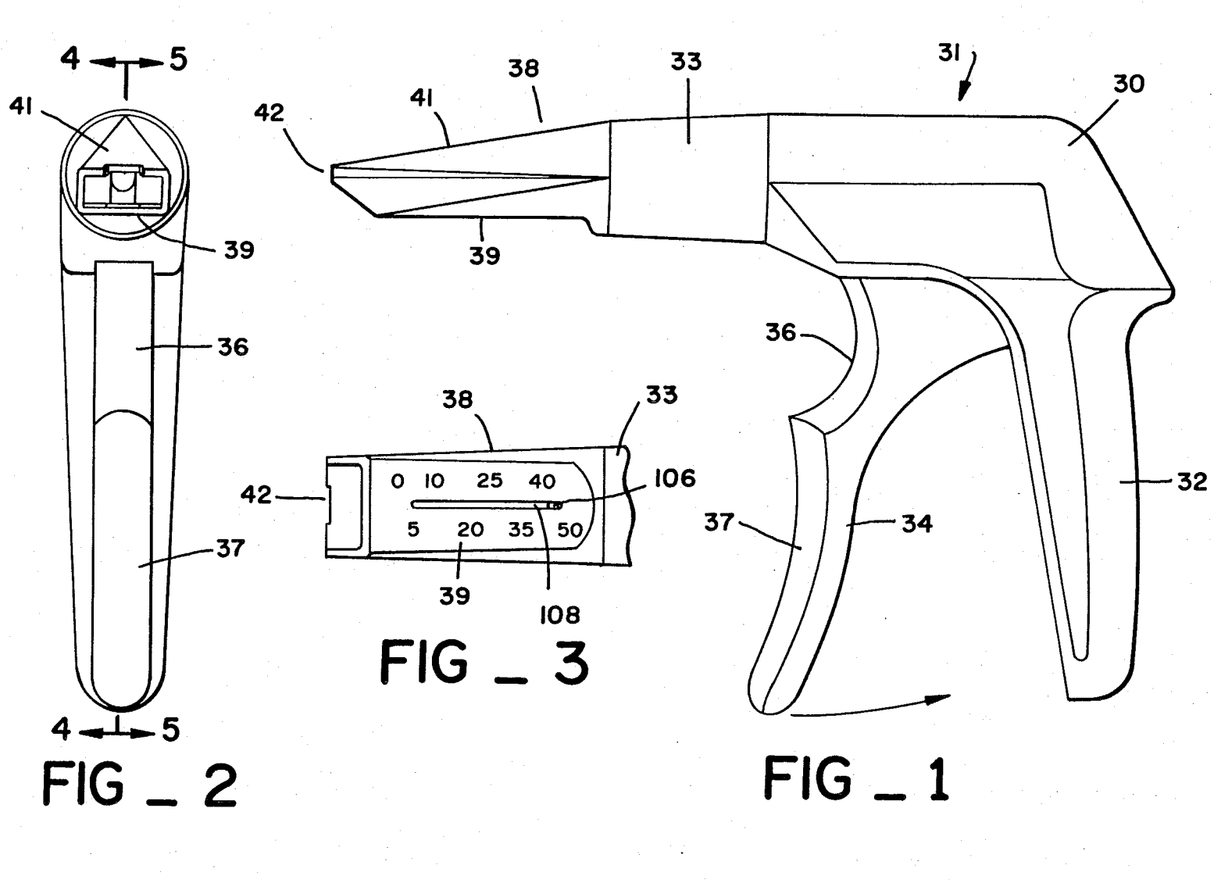
FIG. 1 is a plan view of the surgical staple dispensing and applying tool of the present invention.
FIG. 2 is an end view of the surgical stapling tool shown in FIG. 1.
FIG. 3 is a partial plan view of the dispensing head of the tool depicted in FIGS. 1 and 2, shown in a rotated position.

With regard to FIGS. 1–3, the tool 31 of the present invention includes a handle 32 extending from one end of a housing 30 having a pistol-like configuration, with a snub-nose barrel 33 extending longitudinally and distally from the other end of the housing. A trigger lever 34 extends from the housing 30 in opposition to the handle 32 and including sculptured insets 36 and 37 to accommodate the index finger and remaining fingers, respectively, of the hand wielding the tool. The trigger is adapted to be squeezed to drive the tool to dispense and apply one surgical staple by each full actuating excursion of the trigger.

A significant feature of the tool 31 is the provision of a head portion 38 rotatably secured to the distal end of the barrel 33. The head portion 38 includes longitudinal surfaces 39 and 41 which taper longitudinally and distally from the barrel toward the distal dispensing end 42, where staples are dispensed and applied serially. This feature provides excellent visualization of the delivery end. Furthermore, the surface 39 includes a counter display which clearly indicates the number of surgical staples remaining in the tool magazine housed in the head portion. The head portion is configured about a nominal rotational axis which is substantially coaxial with the barrel 33 of the tool. A significant feature of the tool is that each staple is delivered from the distal end 42 along the longitudinal axis, with the staple legs extending points-first and parallel to the axis. The orientation of the web of each staple with respect to the handle axis of the tool may be selected by rotation of the head portion 38 about the longitudinal axis to any desired angular setting. Thus the hand wielding the tool may be disposed in a comfortable, non-rotated position while the head portion of the tool is rotated and actuated to install a surgical staple at an otherwise difficult angle.

Figure 4:
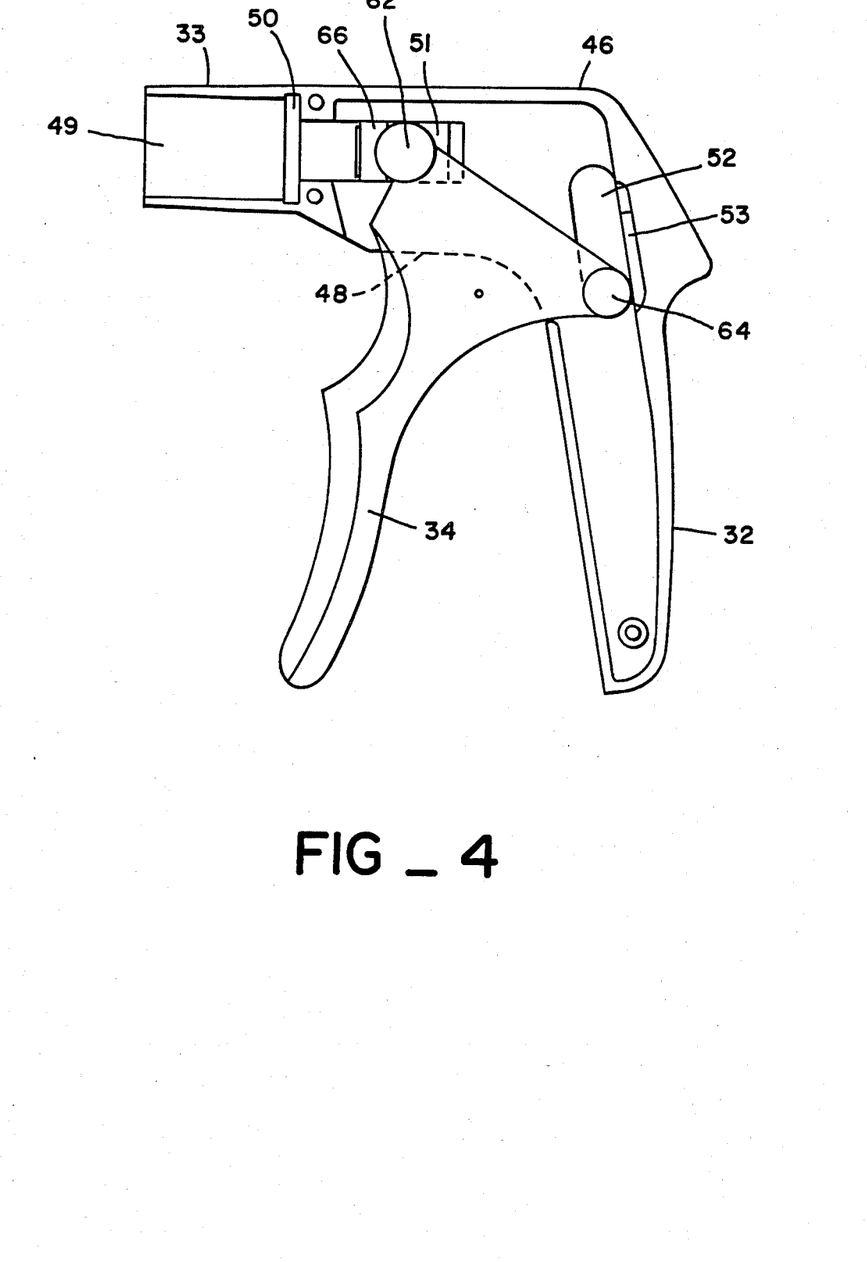
FIG. 4 is a cutaway view of the handle and trigger lever assembly of the present invention, taken along line 4—4 of FIG. 2.
Figure 5:
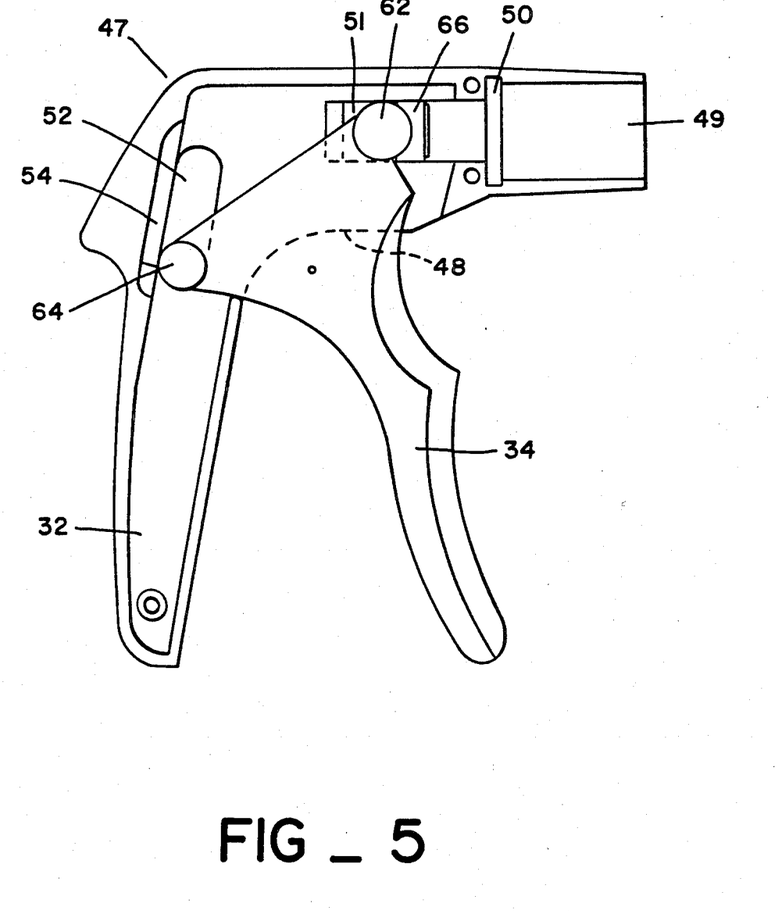
FIG. 5 is a cutaway view of the handle and trigger lever assembly, taken along line 5—5 of FIG. 2.

With reference to FIGS. 4 and 5, the housing 30, handle portion 32, and barrel 33 are all formed integrally together by a pair of housing members 46 and 47. The housing generally comprise molded plastic shells having a clamshell configuration in which each is generally the mirror image of the other, with symmetry about a plane passing through both the longitudinal and handle axes. The housing members define a generally cylindrical bore 49 extending coaxially within the barrel portion 33, with an annular detent recess 50 formed in the proximal end of the bore. The housing members also provide a medial opening 48 for the trigger lever to extend therethrough. A salient feature is the provision of a proximal channel 52 and a distal channel 51 defined by the opposed housing members, each channel comprising a slot-like track. The proximal channel is disposed in the handle portion and is generally parallel to the handle axis, and the distal channel 51 is disposed substantially colinearly with the axis of the bore 49. Indeed, the channel 51 opens into the inner end of the bore.

A significant difference in the housing members 46 and 47 is the provision of a pair of camming tracks 53 and 54, respectively, disposed generally parallel to and partially coextensive with the proximal wall of the channel 52. The camming tracks 53 and 54 are also partially coextensive; however, each includes distinctively configured camming surfaces to perform differing functions, as will be described in the following.

Figures 6, 7, 8:
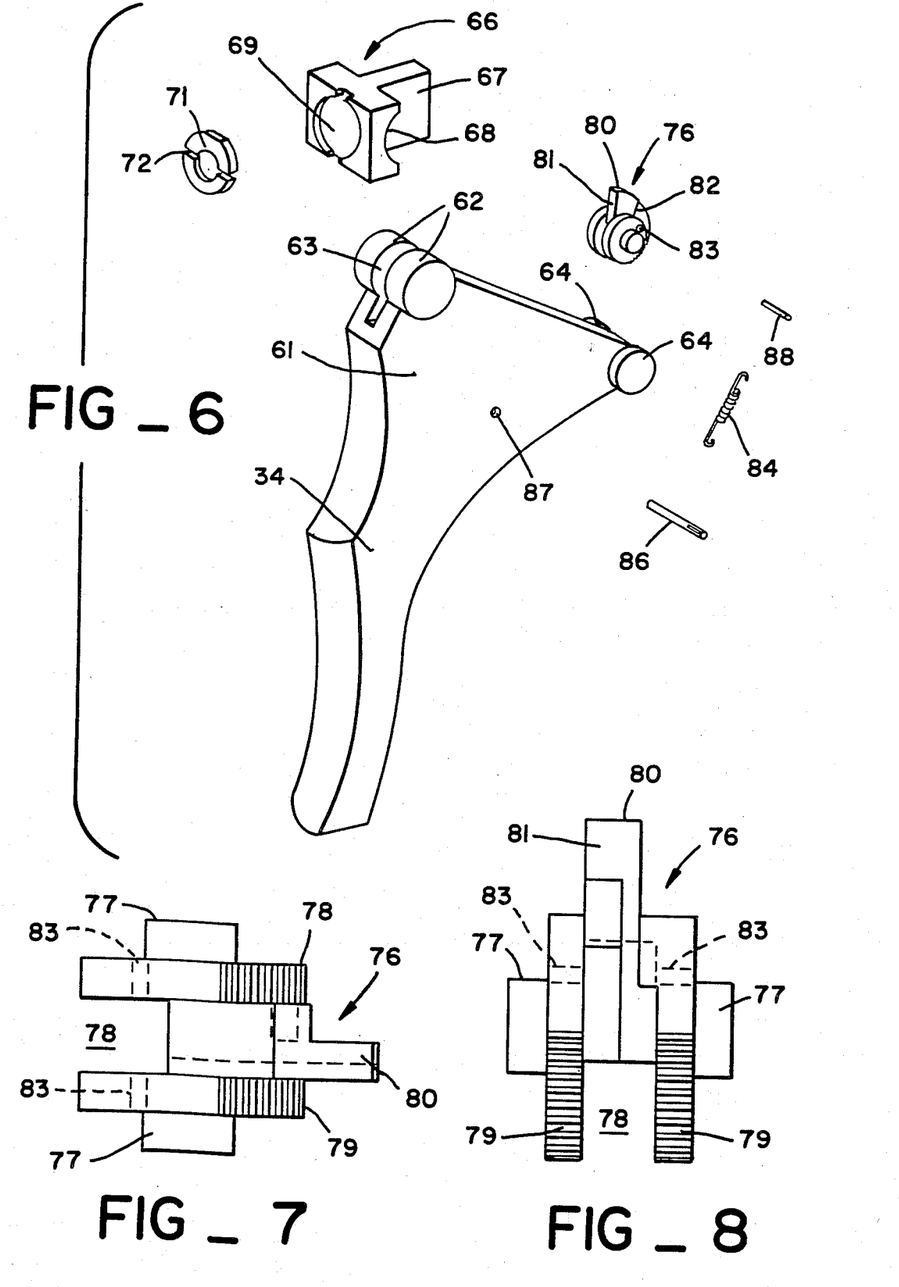
FIG. 6 is an exploded view of the trigger actuating mechanism of the present invention.
FIG. 7 is an enlarged side view of the togle stop member of the trigger actuating mechanism of the present invention.
FIG. 8 is an enlarged side view of the toggle stop member of the trigger actuating mechanism of the present invention.

The trigger actuating means includes the trigger lever 34 extending from a plate 61 oriented generally coextensive with the plane of symmetry of the housing members, as shown in FIG. 6. At the inner distal extent of the plate 61 a pair of generally cylindrical gliding lugs 62 extend from opposed sides of the plate. The axial alignment of the lugs 62 is generally orthogonal to the barrel axis of the tool, and a slot opening 63 extends into the inner distal portion of the plate between the two lugs. The lugs 63 are dimensioned each to be received in one of the channel portions 51 of the respective housing members 46 or 47, and to translate freely therealong in gliding fashion.

Likewise, the inner proximal end of the plate 61 is provided with a pair of generally cylindrical gliding lugs 62 extending from opposed sides of the plate and dimensioned to be received in the respective portion of the channel 52 in gliding, freely translating fashion. The housing members and at least the lug portions of the plate 61 may be fabricated from plastic materials having a low mutual coefficient of friction to facilitate smooth gliding motion of the lugs in the channels. It may be appreciated that the oblique orientation of the channels 51 and 52 determines that the trigger lever describes an arc centered about the translating lugs 62 when the lever is squeezed manually toward the handle 32.

Also disposed in the channel 51 is a driving block 66 which is dimensioned for freely sliding translation in the channel. The block 66 includes a tabular arm extending longitudinally and dimensioned to be received in the slot opening 63 of the trigger plate. The block 66 further includes laterally opposed arcuate recesses 68 opening proximally and dimensioned to receive the distal extents of the pair of lugs 62. As the lever is squeezed and the lugs 62 are translated distally, the driving block is likewise translated distally in the channel 51. The distal end face of the block 66 includes a shallow recess 69 in which a bushing 71 is received in freely rotating fashion. The bushing is disc-like, and includes a slot 72 extending diametrically in the distal end face, for purposes to be described in the following.

An important feature of the trigger actuating mechanism is the provision of a toggle stop member 76, as shown in FIGS. 6–8. The member 76 is generally cylindrical in configuration, and includes a pair of cylindrical knobs 77 extending coaxially from opposed ends thereof. The knobs are dimensioned to be received in suitably formed portions of the channel portions 52. The outer peripheral surface of the member 76 includes a frictional surface 79, comprising a plurality of axially extending toothed ridges, extending partially about the periphery. A slot opening 78 extends radially into the member 76, and is dimensioned to receive a portion of the inner proximal end of the plate 61 therein. A pin 88 is secured in a hole 82 extending parallel to and offset from the axis of the member 76. A pin 86 is secured in a hole 87 in a medial portion of the plate 87, and a tensioning spring 84 is joined in tension between the pins 86 and 88. The spring 84 creates an over-center toggle rotation of the member 76 about the axis of the lugs 77.

A camming member 80 extends radially outwardly from the member 76 and is adapted to translate in freely sliding fashion in the channel portion 53. The camming member 80 is provided with a camming surface 81 which is disposed to impinge on the upper end surface of the channel portion 53 when the trigger lever is completely actuated and the lugs 64 have completely traversed the channel 52. The engagment with the upper end surface applies a counterclockwise rotational moment to the stop member 76, rotating it past the over-center position. This action disengages the friction surface 79 from tending to rotate into engagement with the walls of the channel 52, so that the lugs 64 may slide along the channel 52 on the return excursion of the trigger lever.

The camming member also includes a surface 82 disposed to impinge on the lower end of channel portion 54 when the trigger returns fully to the starting position. This engagement applies a clockwise rotational moment to the stop member 76, rotating it past the over-center position and disposing the frictional teeth 79 to tend to be rotated into the channel surface whenever the handle is partially actuated and then released. The trigger actuating mechanism thus requires a full actuating excursion of the trigger before return motion can begin, and a full return excursion before a new dispensing cycle can be initiated. Thus misfeeding and jamming due to feeding more than one staple at one time is virtually eliminated.

Figure 9:
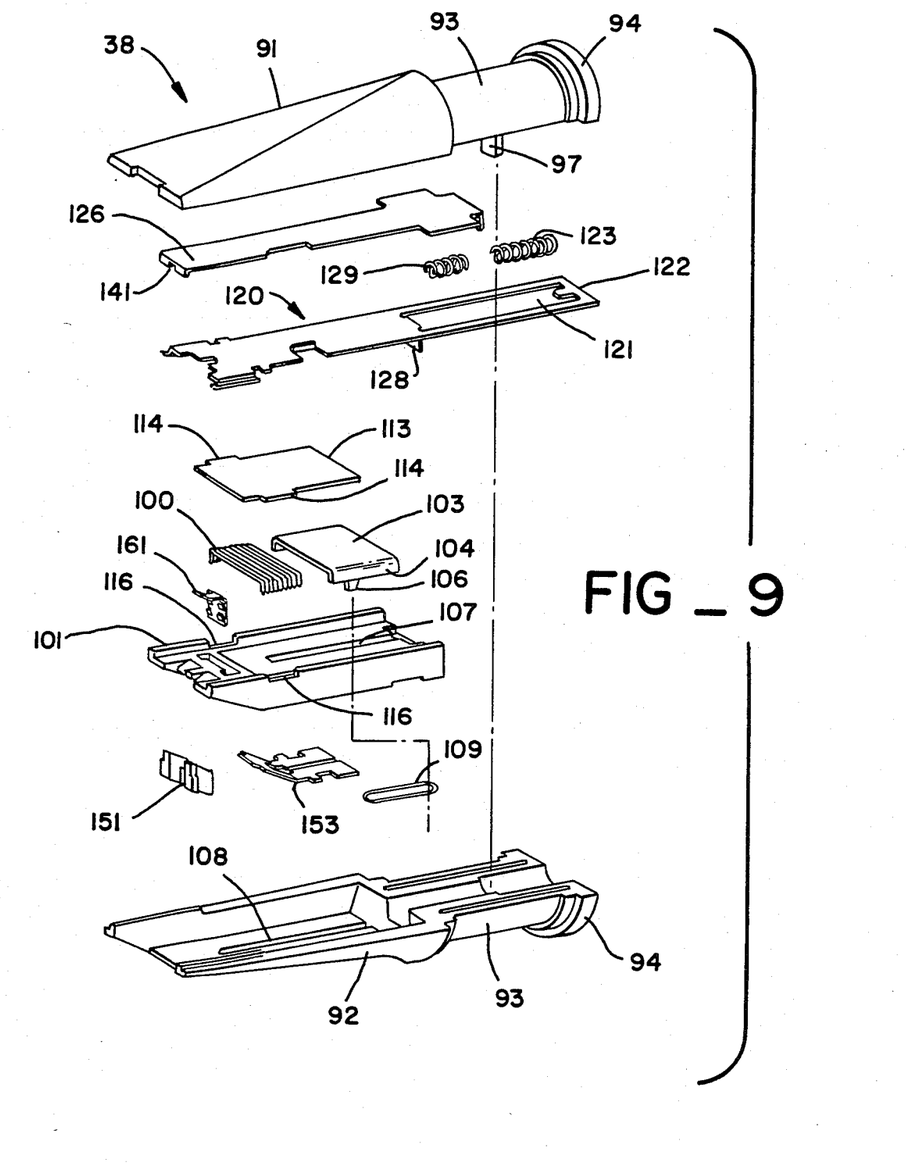
FIG. 9 is an exploded view of the surgical staple dispensing head assembly of the tool of the present invention.

The dispensing head portion 38 of the tool of the present invention includes a pair of opposed housing members 91 and 92 adapted to be joined in clamshell fahsion to define a lingitudinally extending, tapered, closed housing. The proximal end of the housing is comprised of a generally cylindrical neck 93 having a radially extending flange 94 disposed at the proximal end. The neck 93 is dimensioned to be received in the bore 49 of the housing 31 in freely rotating fashion, with the flange 94 being received in the annular groove 50, also in freely rotating fashion. It may be appreciated that the flange secured within the groove retains the dispensing head portion and the housing 31 together in freely rotating fashion about the axis of the bore 49.

Figures 10, 11, 12:
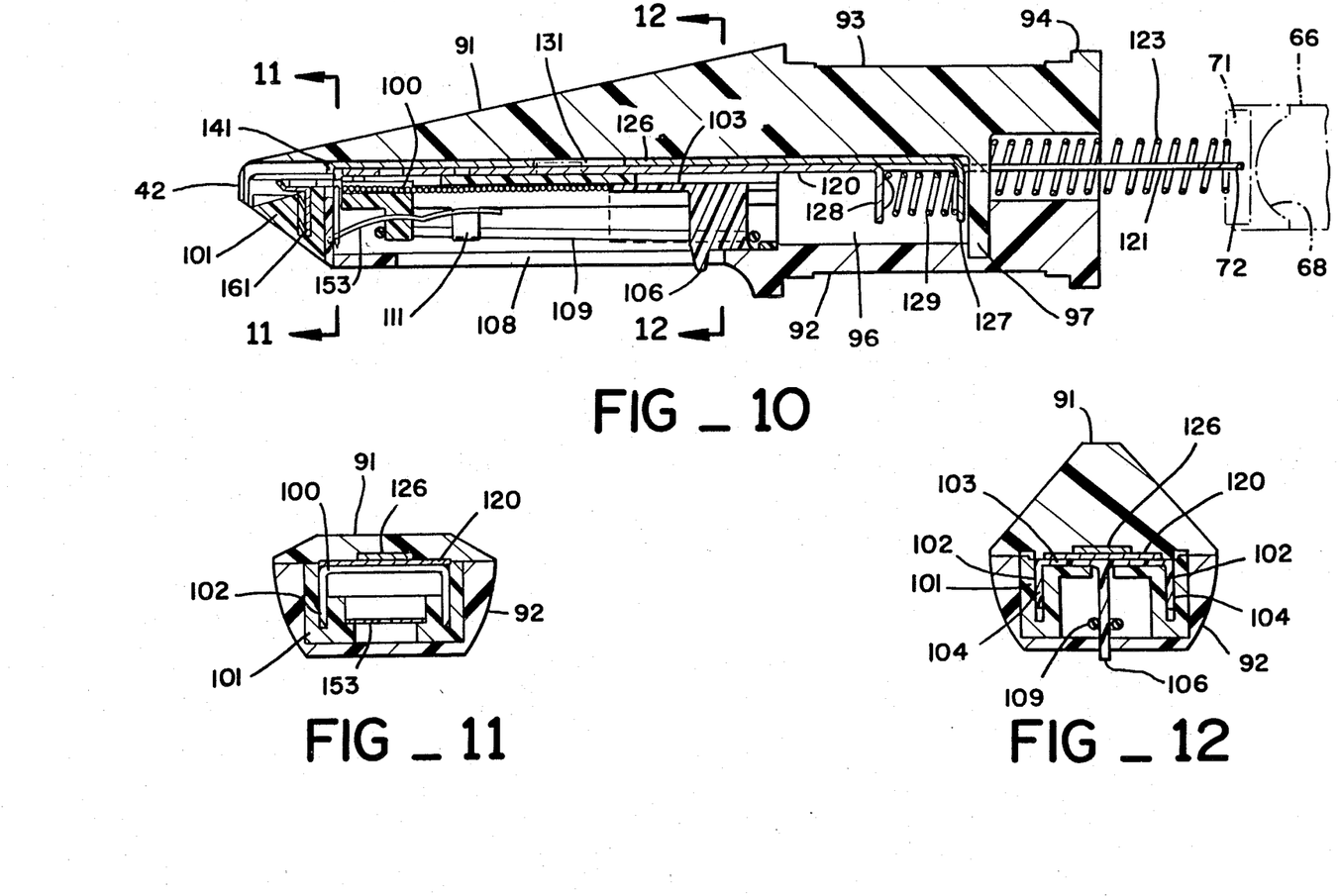
FIG. 10 is a cross-sectional elevation of the dispensing head assembly of the tool of the present invention.
FIG. 11 is a cross-sectional elevation of the dispensing head assembly, taken along line 11—11 of FIG. 10.
FIG. 12 is a cross-sectional elevation of the dispensing head assembly, taken along line 12—12 of FIG. 10.

Within the dispensing head housing, the members 91 and 92 define an interior cavity 96 extending generally longitudinally the length of the dispensing head housing, as shown in FIG. 10. An anchor lug 97 extends from the interior surface of the neck portion 93 of the member 91 into a socket area formed in the opposed housing member 92, for purposes to be explained in the following.

Disposed in the medial to distal portion of the cavity 96 is a surgical staple cartridge or magazine 101. The cartridge includes a pair of parallel, radially spaced staple leg tracks 102 extending longitudinally therein, as shown in FIGS. 9–12. A large plurality of staples 100 is received in the cartridge in parallel, stacked, column fashion, with the legs thereof received in the tracks 102 and adapted for sliding translation longitudinally therealong. A staple column driving member 103 is also provided, including flanges 104 dimensioned to be received in the tracks 102 and a medial panel disposed to engage the medial web portion of the staple column. An indicator wand 106 extends orthogonally from the inner surface of the driving member 103, and is disposed to extend through aligned longitudinal slots 107 in the cartridge body and 108 in the housing member 92. The indicator wand is thus visible from the exterior of the tool, and its position readily noted.

To bias the staple column driving member to translate the staple column longitudinally and distally, an elastic band 109 is secured about the wand 106 at one end and a mounting lug 111 fixed within the cartridge. The tension of the band 109 continuously urges the staple column distally toward the dispensing end 42. Indicia are placed on the exterior surface 39 adjacent to the slot 108, so that the position of the staple driving member may be visualized and the number of staples remaining in the staple column in the tracks 102 may be determined directly. A cover plate 113 is secured atop the staples and staple driver member, with laterally extending tabs received in detents 116 in the opposed sides of the cartridge 101. The cover plate minimizes interference with the other moving parts of the dispensing and forming apparatus.

Another significant feature of the present invention is a form tool 120, comprising a longitudinally extending, generally planar member extending the length of the cavity 96 and extending from the proximal end thereof. The form tool is disposed for reciprocal translation along the longitudinal axis, the inner surfaces of the cavity 96 being configured to comprise guides for the sliding movement. The proximal end portion of the form tool 120 includes a longitudinally extending, closed slot 121 having sufficient width and longitudinal clearance to receive therethrough the fixed lug 97 without interfering with the translation of the form tool.

The proximal end 122 of the form tool 120 is configured to be received in the slot 72 formed in the end surface of the bushing 71 of the trigger actuating mechanism, as shown in FIG. 10. A helical spring 123 is disposed within a portion of the slot 121, extending axially and impinging under compression on the fixed lug 97 and the driving block 66. The spring 123 thus acts to resiliently bias the trigger mechanism to return to the initial, quiescent position, as it is further compressed by any actuating movement of the trigger and the driving block. That is, the trigger translates the driving block 66 and the form tool 120 distally, and the spring 123 urges the driving block and form tool to reciprocate toward the proximal direction.

The dispensing head portion also includes an anvil tool 126 extending longitudinally parallel to the form tool and disposed directly adjacent thereto, as shown in FIGS. 9–14. The anvil tool, which is somewhat shorter in length than the form tool, is adapted for longitudinal reciprocal translation in synchronism with the form tool. The proximal end of the anvil tool includes a flange 127 extending transverse to the longitudinal axis and dimensioned to extend freely through the slot 121. In the initial quiescent disposition the flange 127 abuts the fixed lug 97, which forms a proximal translation stop for the anvil tool. A flange 128 extends from the distal end of the slot 121 of the form tool 120 in spaced opposition to the flange 127, and a compression spring 129 is secured between the two flanges, providing resilient biasing of the relative axial motion of the form tool and anvil tool.

Figure 13:
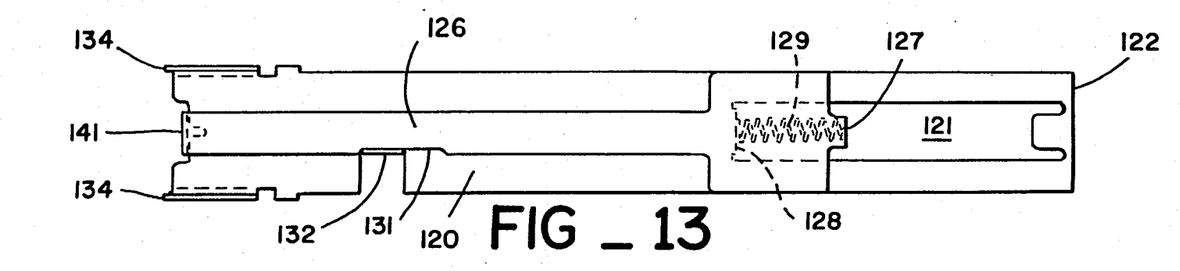
FIG. 13 is a plan view of the form tool and anvil tool assembly of the present invention, shown in the unactuated, quiescent position.
Figures 14, 15, 16, 17, 18:
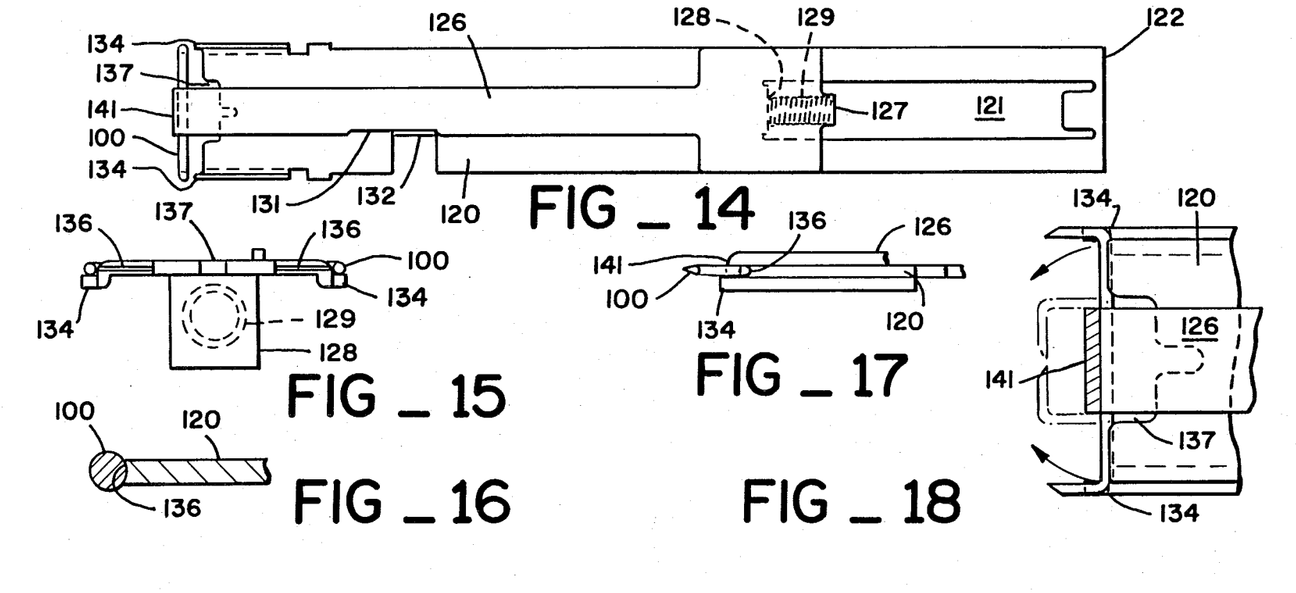
FIG. 14 is a plan view of the form tool and anvil tool assembly of the present invention, shown in an actuated, relatively translated disposition.
FIG. 15 is an enlarged end view of the form tool of the present invention.
FIG. 16 is an enlarged fragmentary view showing the engagement of the form tool and a surgical staple.
FIG. 17 is an enlarged fragmentary view of the form toolanvil tool engagement of a surgical staple.
FIG. 18 is an enalrged plan view of the form tool and anvil tool as depicted in FIG. 17.
Figure 19:
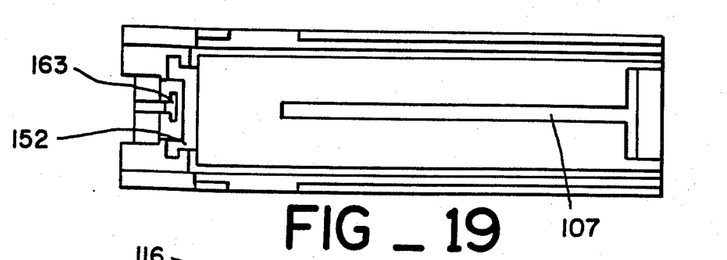
FIG. 19 is a plan view of the cartridge assembly of the tool of the present invention.
Figure 20:
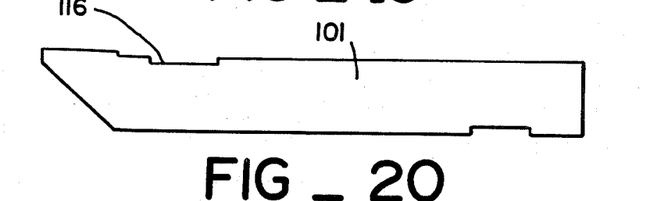
FIG. 20 is a side elevation of the cartridge assembly depicted in FIG. 19.
Figure 21:
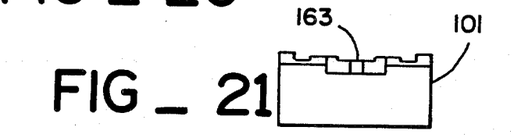
FIG. 21 is an end view of the cartridgee assembly of FIGS. 19 and 20.
Figure 22:
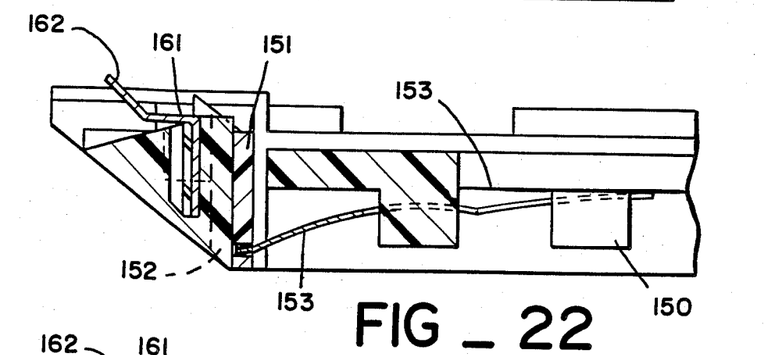
FIG. 22 is a cross-sectional elevation of the dispensing head assembly, showing the staple elevator feed mechanism in the unactuated position.
Figure 23:
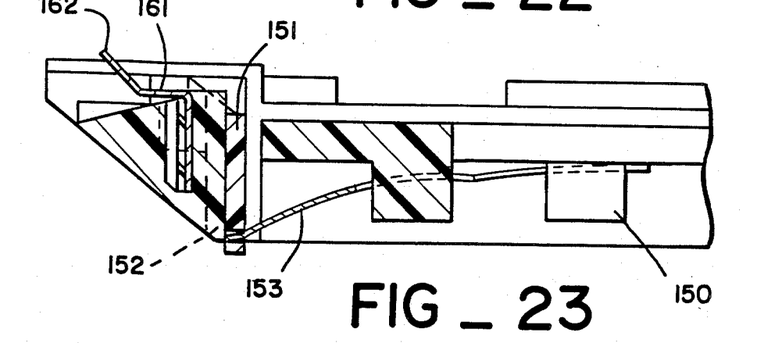
FIG. 23 is a cross-sectional elevation as in FIG. 22, showing the staple elevator feed mechanism in the acutated disposition.

The anvil tool 126 is generally narrower than the form tool 120, and includes a notch 131 formed in an axially extending edge portion thereof. The form tool includes a tab member 132 bent out of the nominal plane of the form tool and disposed to be received in the notch 131. The tab 132 and notch 131 provide precise lost motion drive of the anvil tool by the form tool as it is advanced by the trigger actuating mechanism, as depicted in FIGS. 13 and 14 and described hereinafter.

A salient feature of the form tool are the staple engaging features fashioned at the distal end thereof. The distal edge of the form tool includes a shallow recess 137 extending axially therein, with a pair of grooved staple engaging faces 136 disposed at laterally opposed sides of the recess 137. The arcuate, laterally extending groove 136 is dimensioned to engage the medial web portion of a typical surgical staple, as shown in FIGS. 16–18, and is sufficiently narrow not to engage the staple legs. However, a pair of arms 134 extend longitudinally from the distal end of the form tool 120 and are disposed in spaced parallel relationship. The arms 134 are offset from the nominal plane of the form tool (FIG. 15), and are spaced identically to the spacing of the staple legs. When the form tool advances distally and engages a staple in the dispensing position, the arms 134 first engage the staple legs and apply a rotational moment thereto about the medial web portion of the staple. After the staple has been rotated approximately 90°, the grooved face 136 engages the medial web portion of the staple, and the arms impinge upon and support the sides of the staple legs, as depicted in FIG. 18.

Figure 27:
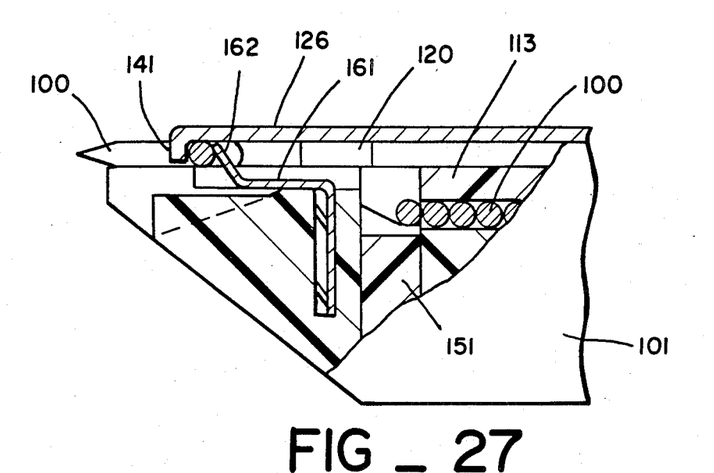
FIG. 27 is an enlarged cross-sectional view of the staple ejector mechanism of the present invention.
Figure 28:
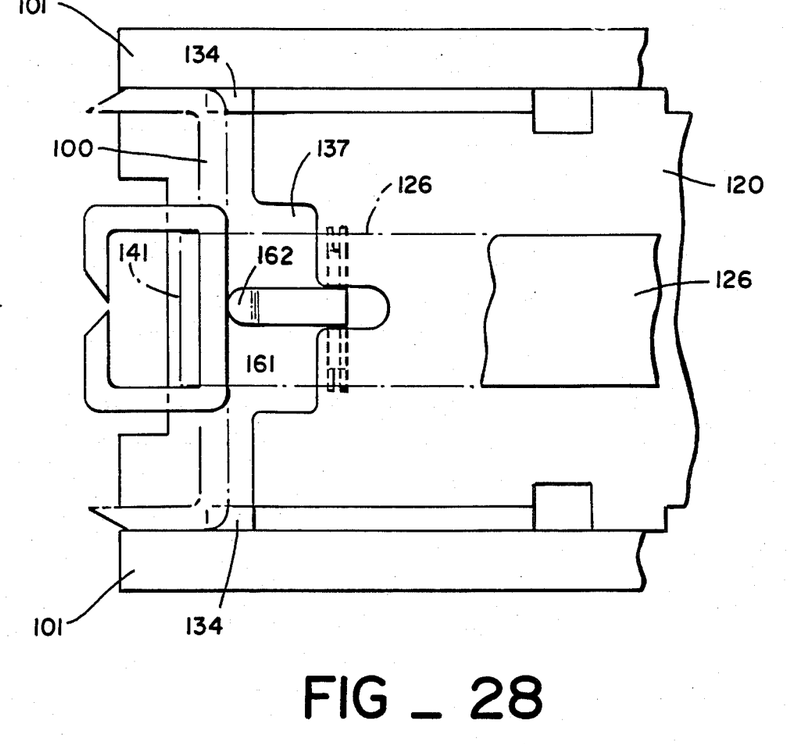
FIG. 28 is an enlarged plan view of the staple ejector mechanism shown in FIG. 27.

The distal end of the anvil tool is provided with an anvil flange 141 which extends distally of the medial web of the staple being dispensed and is opposed tot he driving face 136 of the form tool. The flange 141 is also sufficiently narrow to be freely received in the recess 137 in the distal end of the form tool. The anvil flange serves to impinge on and stabilize the medial web portion of the staple as the arms 134 rotate the staple about the medial web portion. Thus a staple from the column is rotated into a points-first disposition by slight initial advancement of the form tool while the anvil tool remains stationary. Further advancement of the form tool then drives the staple web into the anvil flange, causing the anvil tool to advance together with the form tool toward the distal end. The staple is thus advanced along a linear feed path in the dispensing head while in the grip of the form tool surfaces 136 and the anvil flange 141, as shown in FIGS. 17 and 27.

Another significant feature of the present invention is the provision of a staple elevator member 151, shown in FIGS. 9 and 22–26. The staple elevator member is slidably retained in a suitably formed slot 152 which extends transversely to and intersecting with the staple feed path adjacent to the distal end portion of the tool. A leaf spring 153 extends longitudinally in the tool, with the proximal end secured in a boss 150 disposed adjacent to the magazine and the free distal end engaging the elevator member 151 and biasing it into a blocking position in the staple feed path.

The staple elevator member includes a pair of lugs 154 extending therefrom in laterally spaced disposition, each lug including an obliquely extending ramped surface 156 disposed in mutual coplanar alignment. The space between the lugs 154 provides lateral clearance for the flange 141 of the anvil tool 120. However, the ramped surfaces are disposed to impinge on the medial web portion of a staple being advanced along the feed path when the elevator member is biased by the leaf spring 153 into an interfering position in the feed path. As the form tool and the anvil tool advance the staple being dispensed, the medial web portion of that staple is driven into the ramped surfaces, urging the elevator member 151 to translate in its slot 152 against the resilient force of the spring 153. The elevator member is thus driven out of its blocking disposition in the feed path by the staple itself.

Figures 24, 24A:
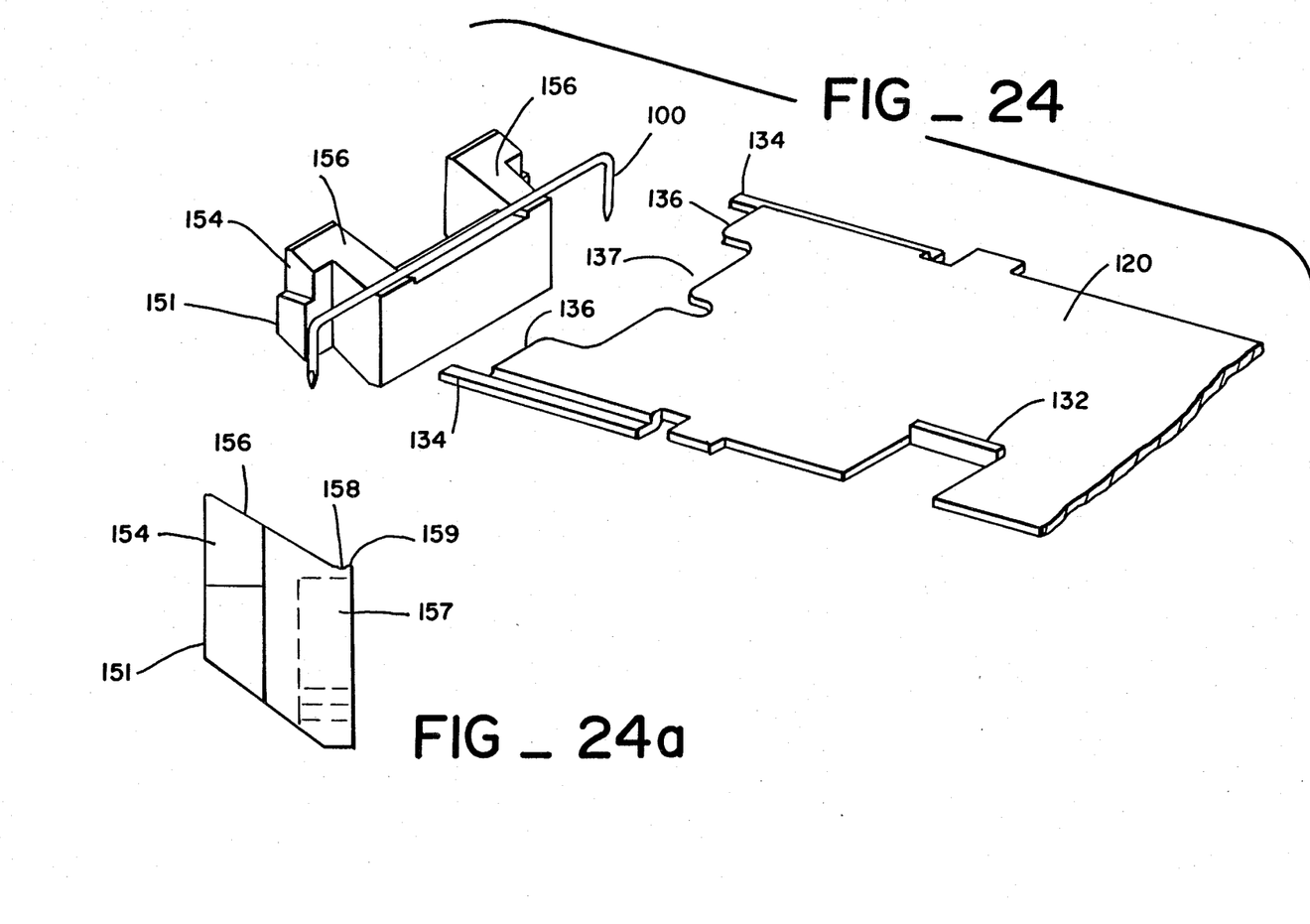
FIG. 24 is a perspective exploded view of the staple elevator feed mechanism of the present invention.
FIG. 24a is an enlarged perspective view of the staple elevator feed member of the present invention.
Figure 25:
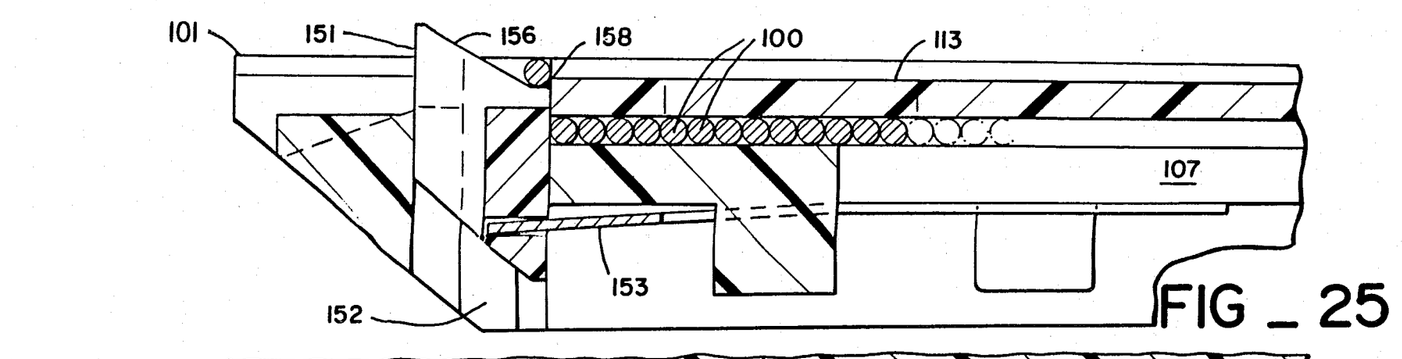
FIG. 25 is an enlarged cross-sectional view of the staple elevator feed mechanism of the present invention.
Figure 26:
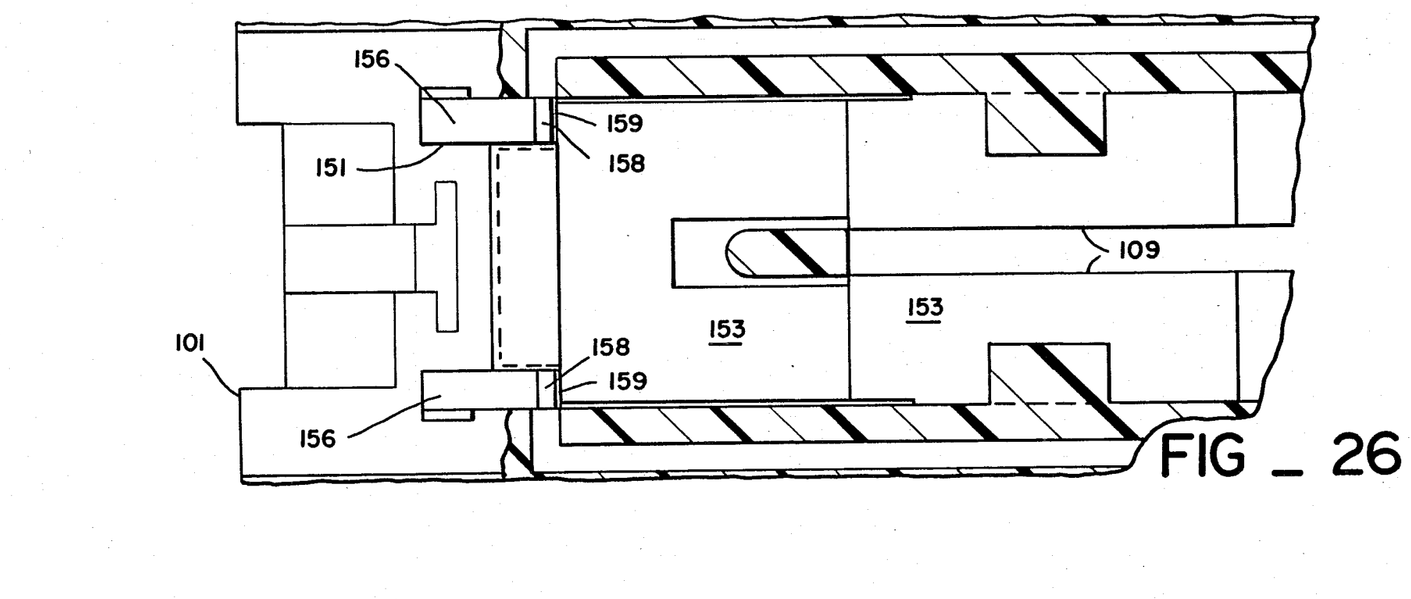
FIG. 26 is a plan view of the staple elevator feed mechanism as shown in FIG. 25.

A salient feature of the elevator member 151 is a nose portion 157 extending proximally therefrom. The nose portion extends proximally a sufficient distance so that, when the elevator member is biased into the blocking position, the nose portion engages the medial web portion of the distal-most staple in the magazine 101. This engagement prevents further distal advancement of the column of staples in the magazine.

The nose portion 157 includes a lateral surface 159 having a shallow laterally extending groove 158 formed therein. When the elevator member is driven out of its blocking position in the feed path by the advancing staple, the advancing form tool prevents the elevator member from returning to the blocking position. During this period the staple column is disengged by the nose portion, and the column advances by the urging of elastic band 109. An integrally formed stop member adjacent to the feed path permits the column to advance only an incremental distance equal to the diameter of one staple. When the form tool is eventually retracted after dispensing and crimping a staple, the elevator member is then free to return to the blocking position. The return motion of the elevator member causes the nose portion to engage the medial web portion of the distal-most staple, which has been advanced with the column. The shallow groove 158 receives the medial web portion of the newly engaged staple, and the return motion of the elevator shears that staple from the column and translates it transversely with respect to the column and into the dispensing position where the medial web portion of that staple is aligned between the flange 141 of the anvil tool and the arms 134 of the form tool. This staple is thus disposed to be dispensed in the next dispensing cycle.

After cleaning and translating past the elevator member, the form tool advances the staple and the anvil tool along the linear feed path to the distal end of the tool. The anvil toolthen abuts an integral stop in the tool, while the form tool is free to continue translation distally. At this point the staple legs are fully extending, points-first, from the distal end. Thus the surgeon may clearly visualize the entry points of the staple points in the skin, or other tissue. Indeed, even if the grip of the surgeon's hand on the trigger lever is relaxed, the toggle stop member will maintain the form tool and anvil tool in this position with the staple extended outwardly.

Further squeezing of the trigger lever from this position will further advance the form tool, driving the medial web portion of the staple against the flange 141, which is immobilized. The surfaces 136 drive the opposed end portions of the web, while the medial portion is also immobilized. The advancing form tool receives the flange in the recess portion 137, and the staple web is crimped at the laterally opposed edges of the flange 141. The staple legs are driven laterally inwardly each toward the other, crimping the staple legs into the tissue and forming a rectangular configuration of the staple.

Another important feature of the present invention is the provision of an ejector spring 161 fixedly secured in a slot 163 in the distal end of the tool, as shown in FIGS. 19, 22, 23, 27, and 28. The ejector spring includes a finger 162 extending obliquely upwardly into the feed path and inclined distally. The oblique orientation of the finger 162 permits the flange 141, the staple being dispensed, and the anvil tool to deflect the finger 162 during distal advancement of the staple without any engagement thereof. However, after the staple has been fully crimped and the trigger lever is released, the form tool and anvil tool initiate proximal return motion by the resilient force of springs 123 and 129. As this proximal return motion begins, the oblique orientation of the finger 162 and its resilient force caused by deflection during advancement causes it to interject in the space between the medial web of the crimped staple and the inner extend of the recess 137 of the form tool, as shown in FIG. 27. The oblique orientation of the finger 162 also causes it to drive the staple web out of engagement with the flange 141, releasing the staple from the anvil tool and, indeed, from the tool inself. Thus the user of the present invention need not undertake any special precedure to separate the crimped staple from the tool, other than releasing the trigger after crimping is completed.

It may be appreciated that the tool of the present invention provides an easy and virtually failsafe mechanism for storing, dispensing, and applying surgical staples. The method of the present invention generally involves the operation of the tool as described herein.

We claim:

1. A surgical stapling device, including means for storing a pluality of surgical staples in a parallel, stacked column extending along a longitudinal axis, means for separating the endmost staple of said stacked column therefrom, means for engaging the legs of said endmost staple in torque applying fashion for rotating said endmost staple to a points-first orientation along an axis parallel to said longitudinal axis, and means for crimping and securing the rotated staple.

2. The surgical stapling device of claim 1, wherein said device includes a barrel portion extending generally along said longitudinal axis, and a handle extending from the proximal end of said barrel portion in pistol-like configuration.

3. The surgical stapling device of claim 2, wherein said means for rotating includes form tool means extending longitudinally within said barrel portion and including portions adapted to engage the legs of said endmost staple in said torque applying fashion.

4. The surgical stapling device of claim 3, wherein said means for storing includes a staple magazine extending longitudinally within said barrel portion and generally adjacent to said form tool means.

5. The surgical stapling device of claim 4, further including a staple feed path extending from the distal end of said staple magazine to the distal end of said barrel portion, and means for translating said form tool means along said staple feed path in reciprocal fashion.

6. The surgical stapling device of claim 5, wherein said form tool means includes a form tool extending longitudinally in said barrel portion, said form tool including end surface means for engaging, rotating, and thereafter translating said separated staple along said feed path.

7. The surgical stapling device of claim 6, wherein each surgical staple includes a web portion and a pair of legs extending from opposed ends of said web portion, said end surface means of said form tool including a pair of arms extending distally therefrom and disposed to initially contact the legs of said separated staple and rotate said separated staple about the web portion thereof.

8. The surgical stapling device of claim 7, wherein said end surface means of said form tool further includes driving surface means adapted to engage the web portion of said rotated staple and to urge said rotated staple distally along said feed path.

9. The surgical stapling device of claim 8, further including anvil tool means extending longitudinally in said barrel portion and disposed generally adjacent and parallel to said form tool, said anvil tool means adapted for reciprocal translation in said barrel portion in concert with said form tool.

10. The surgical stapling device of claim 9, wherein said anvil tool means includes a distal end portion with flange means extending therefrom, said flange means adapted to engage the web portion of said separated and rotated staple in distal opposition to the proximal position of said end surface means of said form tool.

11. The surgical stapling device of claim 10, further including means for translating said form tool longitudinally and reciprocally along said barrel portion.

12. The surgical stapling device of claim 11, further including linking means extending between said form tool and said anvil tool means for driving said anvil tool means longitudinally and reciprocally in concert with said form tool.

13. The surgical stapling device of claim 12, wherein said linking means includes compression spring means extending between said form tool and said anvil tool means.

14. The surgical stapling device of claim 13, further including means for crimping said separated and rotated staple, comprising said flange means engaging a medial portion of a distal surface of the web portion of said separated and rotated staple, said driving surfaces engaging opposed end portions of a proximal surface of the web portion of said separated and rotated staple, stop means for preventing distal translation of said anvil tool means at a predetermined position, and means for advancing said form tool distally past said predetermined position to cause said driving surfaces to crimp said web portion about said flange means.

15. The surgical stapling device of claim 14, further including finger spring means for disengaging said crimped staple from said flange means and said driving surface means of said form tool.

16. The surgical stapling device of claim 15, wherein said finger spring means includes a finger spring extending distally and obliquely in said barrel and disposed to be deflected by said form tool and flange means translating distally thereby and to interject between said driving surfaces and said web portion of said crimped staple as said form tool and anvil tool means return proximally to disengage said web portion therefrom.

17. The surgical stapling device of claim 2, wherein said barrel portion includes a proximal barrel portion fixed to said handle portion, and a distal barrel portion secured to said proximal barrel portion in rotatable fashion about said longitudinal axis.

18. The surgical stapling device of claim 17, wherein said means for storing a plurality of surgical staples in a parallel, stacked column extending along a longitudinal axis, said means for separating the endmost staple of said stacked column therefrom, said means for rotating said endmost staple to a points-first orientation along said longitudinal axis, and said means for crimping and securing the rotated staple are all disposed and secured in said distal, rotatable barrel portion.

19. The surgical stapling device of claim 18, wherein said means for storing a plurality of surgical staples includes means for indicating the number of staples remaining in said parallel, stacked column.

20. The surgical stapling device of claim 19, further including a column driving member adapted to engage the proximal end of said column of staples, and resilient means for urging said column driving member and said staple column distally along said longitudinal axis.

21. The surgical stapling device of claim 20, further including an indicator slot formed in said distal portion of said barrel, and an indicator wand extending from said column driving member through said indicator slot and disposed to be visible from the exterior of said distal barrel portion.

22. The surgical stapling device of claim 21, further including numerical indicia means extending adjacent to said indicator slot and said indicator wand extending therefrom, said numerical indicia being spaced in correspondence with the position of said wand and the number of staples remaining in said column.

23. The surgical stapling device of claim 11, wherein said means for driving said form tool include trigger actuating means.

24. The surgical stapling device of claim 23, wherein said trigger actuating means includes a trigger lever extending from said barrel portion in adjacent opposition to said handle portion.

25. The surgical stapling device of claim 24, further including a trigger plate from which said trigger lever extends.

26. The surgical stapling device of claim 25, wherein said trigger plate includes opposed ends and at least one pair of gliding knobs, each secured to one of said opposed ends in spaced apart, opposed relationship.

27. The surgical stapling device of claim 26, further including a pair of guide channels in said device, each of said guide channels adapted to receive and secure one of said gliding knobs in freely translating fashion.

28. The surgical stapling device of claim 27, wherein said guide channels are obliquely oriented within the same general plane, whereby translation of said gliding knobs in said guide channels causes rotational and translational movement of said trigger plate.

29. The surgical stapling device of claim 28, wherein one of said opposed ends of said trigger plate is disposed distally of the other.

30. The surgical stapling device of claim 29, further including a driving block engaged with said gliding knob at said distal end of said trigger plate, said driving block disposed to be driven in reciprocal translational motion by movement of said trigger plate by said trigger lever.

31. The surgical stapling device of claim 30, wherein said driving block includes means for engaging the proximal end of said form tool and driving said form tool in reciprocal translational motion along said longitudinal axis.

32. The surgical stapling device of claim 29, further including means for requiring full translation of one of said gliding knobs in its respective guide channel along the entire length thereof in one direction before said gliding knob may return in the opposite direction along said guide channel.

33. The surgical stapling device of claim 32, wherein said means for requiring full translation includes a track formed adjacent to one of said guide channels, and a toggled brake member disposed in said track.

34. The surgical stapling device of claim 33, wherein said toggled brake member is rotatably secured to said trigger plate and adapted for translational movement along said track.

35. The surgical stapling device of claim 34, wherein said toggled brake member includes frictional surface means disposed to engage a surface of said track and prevent reverse translation of said toggled brake member.

36. The surgical stapling device of claim 35, wherein said track further includes camming surface means at both ends thereof to rotate said toggled brake member and permit reverse translation from one end to the other.

37. A trigger actuating mechanism for a tool, comprising;
a trigger lever extending from said tool in adjacent opposition to a handle portion, a trigger plate from which said trigger lever extends, said trigger plate including opposed ends and at least one pair of gliding knobs, each secured to one of said opposed ends in spaced apart, opposed relationship, a pair of guide channels formed in said tool, each of said guide channels adapted to receive and secure one of said gliding knobs in freely translating fashion, said guide channels being diposed within the same general plane and oriented along intersecting axes, whereby movement of said trigger lever toward said handle portion causes translation of said gliding knobs in said guide channels and rotational and translational movement of said trigger plate.

38. The trigger actuating mechanism of claim 37, wherein one of said opposed ends of said trigger plate is disposed distally of the other with respect to the longitudinal axis of the tool.

39. The trigger actuating mechanism of claim 38, further including a driving block engaged with said gliding knob at said distal end of said trigger plate, said driving block disposed to be driven in reciprocal translational motion by movement of said trigger plate by said trigger lever.

40. The trigger actuating mechanism of claim 39, wherein said driving block includes means for engaging the proximal end of work engaging member and driving said member in reciprocal translational motion along said longitudinal axis.

41. A method for surgical stapling, comprising the steps of: storing a plurality of surgical staples in parallel, stacked column fashion, said column extending along an axis, non-rotably separating the endmost surgical staple from one end of said column, directly impinging on the legs of the separated staple to rotate the separated staple into a points-first orientation along an axis parallel to said column axis, and crimping said separated staple to secure said separated staple at a surgical site.

42. A surgical stapling device, including means for storing a plurality of surgical staples in a parallel, stacked column with like web portions of said staples extending in a common plane, means for separating the endmost staple of said stacked column therefrom and translating said endmost staple transversely from said common plane to a feed path; means in said feed path for directly impinging on and rotating said endmost staple to a points-first orientation along said feed path, and means for advancing and crimping the rotated staple.

43. A surgical stapling device, including means for storing a plurality of surgical staples in a parallel, stacked column extending along a longitudinal axis, dispensing means for rotating the endmost staple to a points-first orientation along an axis parallel to said longitudinal axis and thereafter advancing and crimping the rotated staple, and elevator means for separating and shifting the endmost staple of said column out of axial alignment with said column to engagement with said dispensing means, said elevator means being operated by the advancement and retraction of said dispensing means.

44. A surgical stapling device, including means for storing a plurality of surgical staples in a parallel, stacked column with like web portions of said staples extending in a common plane, manually actuable means for dispensing a staple from said column and advancing and crimping the staple in a reiterative stapling cycle, means operable once each stapling cycle for non-rotatably separating the endmost staple of said stacked column therefrom and driving said endmost staple transversely from said common plane to a feed path; means in said feed path for directly impinging on and rotating said endmost staple to a points-first orientation along said feed path, and means for advancing and crimping the rotated staple.

45. A surgical stapling device, including means for storing a plurality of surgical staples in a parallel, stacked column extending along a longitudinal axis, means for separating the endmost staple of said stacked column therefrom, means for rotating, advancing, and crimping the separated staple, including a reciprocally translating form tool extending generally parallel to said axis and including first surface means for initially contacting the staple legs and rotating the separated staple, second surface means for thereafter contacting the staple web and translating the separated staple; further including an anvil tool extending generally parallel to said axis and adapted for reciprocal translation in concert therewith, said anvil tool including an anvil disposed to translate in advance of the staple web and to impinge thereupon.

* * * * *